United States Patent [19]

Russell

[11] Patent Number: 5,691,313
[45] Date of Patent: Nov. 25, 1997

[54] METHODS OF TREATING IMPOTENCY WITH CILIARY NEUROTROPHIC FACTOR

[75] Inventor: Deborah A. Russell, Thousand Oaks, Calif.

[73] Assignee: Amgen Inc., Thousand Oaks, Calif.

[21] Appl. No.: 704,479

[22] Filed: Aug. 26, 1996

Related U.S. Application Data

[63] Continuation of Ser. No. 298,442, Aug. 29, 1994, abandoned, which is a continuation-in-part of Ser. No. 735,538, Jul. 23, 1991, abandoned.

[51] Int. Cl.$^6$ ................................................ A61K 38/18
[52] U.S. Cl. ................................................ 514/12; 514/2
[58] Field of Search ................................ 530/350, 399; 514/2, 12; 435/69.1, 69.4

[56] References Cited

U.S. PATENT DOCUMENTS 5,011,914  4/1991  Collins et al. ........................ 530/399

OTHER PUBLICATIONS

Heaton, J.P.W. et al., *J. Urol.*, 145(5):1099–1102, 1991.
Lerner, S.E. et al., *J. Urol.*, 149 (5 Part 2):1246–55, 1993.

*Primary Examiner*—Marianne P. Allen
*Attorney, Agent, or Firm*—Ron K. Levy; Steven M. Odre

[57] ABSTRACT

The present invention provides methods for treating impotency with the use of a therapeutically effective amount of ciliary neurotrophic factor (CNTF). Pharmaceutical compositions containing CNTF in a pharmaceutically acceptable carrier are also provided.

5 Claims, No Drawings

METHODS OF TREATING IMPOTENCY WITH CILIARY NEUROTROPHIC FACTOR

CROSS REFERENCE TO RELATED APPLICATIONS

This application is a continuation of application Ser. No. 08/298,442, filed Aug. 29, 1994 now abandoned which is a continuation-in-part of U.S. patent application Ser. No. 07/735,538, filed Jul. 23, 1991, now abandoned.

BACKGROUND OF THE INVENTION

The present invention is directed to methods for the prevention and treatment of impotency by administering neurotrophic factors, particularly ciliary neurotrophic factor (CNTF).

Neurotrophic factors are naturally occurring proteins that promote the survival and functional activities of nerve cells. These factors have been found in the target cells to which an innervating nerve cell connects. Such target-derived neurotrophic factors regulate the number of contacts formed between innervating nerve cells and the target cell population, and are necessary for the survival and maintenance of these nerve cells.

Neurotrophic factors are also found in cells that are not innervated. An example of such a neurotrophic factor is CNTF. Human CNTF and the gene encoding human CNTF are described in detail in U.S. Pat. No. 4,997,929, and U.S. Pat. No. 5,141,856. Although the biological role of CNTF has not been conclusively established, CNTF appears to be released upon injury to the nervous system and may limit the extent of injury or neuronal damage.

Highly purified CNTF has been shown to support the survival in cell cultures of chick embryonic parasympathetic, sympathetic, sensory, and motor neurons. There is evidence to support that CNTF is a neurotrophic factor for peripheral primary neurons in vive and in vitro. However, there has been no evidence linking CNTF to the mediation of central effects in the hypothalamus, a brain region that is involved in integration of sexual behavior, and no evidence indicating that the subcutaneous administration of CNTF causes any change in brain physiology.

In humans as well as in rats and non-human primates, penile erection has been associated centrally with dopaminergic receptor activation and peripherally with inhibition of α adrenergic influences and stimulation of β adrenergic and nonadrenergic/noncholinergic influences as described in *Arch. Gen. Psychiatry*, 46:275 (1989). Sensory and motor neurons of the somatic system are also involved in erection according to Carrier et al., *Urology*, 42:468–481 (1993). Sensory impulses from the penile skin and glans penis are transmitted via the dorsal, pudendal, and sacral nerves to the spinal cord. The pudendal motor neurons arise from Onuf's nucleus in the second to fourth sacral spinal segment and control ischiocavernosus and bulbospongiosus muscle tone to produce full rigidity during erection.

The identity of the principle penile neurotransmitter is unknown. Candidate neurotransmitters include acetylcholine, a calcitonin-gene related peptide, substance P, neuropeptide Y and vasoactive intestinal polypeptide (VIP). These neurotransmitters induce erection when injected intracavernously in human volunteers or in animals and are released during neurostimulation-induced erection. Theoretically, defects in the release or synthesis of neurotransmitters could inhibit erectlie function.

Centrally, the medial preoptic area of the hypothalamus is believed to be an important integration center for sexual drive and penile erection. Apomorphine, oxytocin, and bromocryptine are well know inducers of erection in both humans and animals and are believed to act at the hypothalamus via a dopaminergic mechanism.

Impotency is defined as a consistent inability to achieve or maintain penile erection that is adequate for completion of sexual intercourse. Ten million American men are estimated to be afflicted with this condition. Impotency may result from dysfunction in a number of systems. Its origin may be hormonal, vascular, neurogenic, cavernosal or psychogenic or may be secondary to other systemic diseases. Treatment of impotency is often directed toward these underlying causes, but such treatment is frequently ineffective. For example, there are an estimated two million cases of impotency of organic etiology resulting from diabetes mellitus despite therapy with insulin.

Accordingly, a need exists for alternative methods to treat impotency. The present invention satisfies this need and provides related advantages as well.

SUMMARY OF THE INVENTION

The present invention provides methods for the prevention and treatment of sexual dysfunction in males by administering a human protein ciliary neurotrophic factor to a patient in need thereof. In particular, the invention provides methods for administering therapeutically effective amounts of CNTF by effective routes of administration to treat impotency.

The present invention further provides pharmaceutical compositions containing a therapeutically effective amount of CNTF in a pharmaceutically-acceptable carrier.

DETAILED DESCRIPTION OF THE INVENTION

Reference will now be made in detail to the presently preferred embodiments of the invention, which, together with the following examples, serve to explain the principles of the invention.

The present invention provides methods for treating sexual dysfunction in a male patient by administering to that patient neurotrophic factor CNTF, preferably recombinant human CNTF (rhCNTF).

In one embodiment of this invention, preferred CNTFs are naturally occurring proteins. The naturally-occurring proteins are preferred in part because they are believed to pose a lower risk of producing unforeseen and undesirable physiological side effects in patients treated therewith. However, to the extent that non-human CNTFs are substantially equivalent to human CNTFs and possess equivalent biological activity, they are considered to be within the scope of this invention.

For purposes herein, a protein is deemed to be "naturally-occurring" if it or a substantially equivalent protein can be found to exist normally in healthy humans. "Naturally-occurring" proteins specifically include forms of proteins found to exist in healthy humans that are partially truncated at the amino or carboxyl terminus of such proteins or that have amino acids that are deamidated or otherwise chemically modified. "Naturally-occurring" proteins may be obtained by recombinant DNA methods as well as by isolation from cells which ordinarily produce them. "Naturally-occurring" also encompasses proteins that contain or lack an $NH_2$-terminal methionyl group as consequence of expression *E. coli*.

"Substantially equivalent" as used throughout the specification and claims is defined to mean possessing a very high degree of amino acid residue homology (See generally M. Dayoff, *Atlas of Protein Sequence and Structure*, vol. 5, p. 124 (1972), National Biochemical Research Foundation, Washington, D.C., specifically incorporated herein by reference) as well as possessing comparable biological activity.

Particularly preferred CNTFs of the present invention are the naturally-occurring proteins that have previously been described in U.S. Pat. No. 5,141,856, which is specifically incorporated herein by reference. Other preferred forms of CNTF are described in U.S. patent application Ser. No. 07/753,176 filed Aug. 30, 1992 now abandoned of Collins et al. (the "'176 application"), which is entitled "Purification of Recombinant Ciliary Neurotrophic Factor and C-Terminal Truncated Ciliary Neurotrophic Factor," which is also specifically incorporated herein by reference.

The nucleic acid sequences of the genes encoding human and animal CNTFs and the amino acid sequences of such proteins are given in the '176 application. The present invention encompasses non-glycosylated forms of CNTF as well as truncated forms of the naturally-occurring and recombinant CNTF proteins as also described in the '176 application. In a further embodiment, CNTF is modified by attachment of one or more polyethylene glycol (PEG) or other repeating polymeric moieties.

Methods for producing CNTFs are also disclosed in the '176 application. One disclosed method consists of isolating CNTF from various sources, such as peripheral nerve tissues. A second disclosed method involves isolating the genes responsible for coding CNTF, cloning the gene in suitable vectors and cell types, and expressing the gene in order to produce the CNTF. The latter method, which is exemplary of recombinant DNA methods in general, is a preferred method of the present invention. Recombinant DNA methods are preferred in part because they are capable of achieving comparatively higher amounts of proteins with greater purity.

Preferably, the above described CNTFs are produced by the aforementioned method in "substantially pure" form. By "substantially pure" it is meant that CNTF, in an unmodified form, has a comparatively high specific activity. It is to be recognized, however, that derivatives of CNTF may have different specific activities.

Because it is possible that the treatment or prevention of impotency with CNTF is imparted by one or more discrete and separable portions of the CNTF protein, it is also envisioned that the method of the present invention could be practiced by administering a therapeutic composition whose active ingredient consists of that portion (or those portions) of CNTF which controls (or control) CNTF function in treating impotency.

In a preferred embodiment of the present invention, a pharmaceutical composition comprising CNTF is administered in an effective amount to patients in order to treat impotency. For therapeutic applications, CNTF can be formulated in a pharmaceutically-acceptable carrier to produce pharmaceutical compositions. The term "pharmaceutically acceptable carrier" as used herein means a non-toxic, generally inert vehicle for the active agent, which does not adversely affect the agent or the patient to whom the composition is administered. Suitable vehicles or carriers can be found in standard pharmaceutical texts, for example, in *Remington's Pharmaceutical Science*, 16th ed., Mack Publishing Co., Easton, Pa. (1980), incorporated herein by reference. Such carriers include, for example, aqueous solutions such as bicarbonate buffers, phosphate buffers, Ringer's solution and physiological saline. In addition, the carrier can contain other pharmaceutically-acceptable excipients for modifying or maintaining the pH, osmolarity, viscosity, clarity, color, sterility, stability, rate of dissolution, or odor of the formulation.

The pharmaceutical compositions can be prepared by methods known in the art, including, by way of an example, the simple mixing of reagents. Those skilled in the art will know that the choice of the pharmaceutical carrier and the appropriate preparation of the composition depend on the intended use and mode of administration.

In one embodiment, it is envisioned that the carrier and CNTF as the active agent constitute a physiologically-compatible, slow-release formulation. It is possible to control the rate of release of the active agent(s) by proper choice of labile linking groups in the oligonucleotide, which would be known to those skilled in the art. The primary solvent in such a carrier can be either aqueous or non-aqueous in nature. In addition, the carrier can contain other pharmacologically-acceptable excipients for modifying or maintaining the pH, osmolarity, viscosity, clarity, color, sterility, stability, rate of dissolution, or odor of the formulation. Similarly, the carrier can contain still other pharmacologically-acceptable excipients for modifying or maintaining the stability, rate of dissolution, release, or absorption of the active agents. Such excipients are those substances usually and customarily employed to formulate dosages for parenteral administration in either unit dose or multi-dose form.

Once the pharmaceutical composition has been formulated, it can be stored in sterile vials as a solution, suspension, gel, emulsion, solid, or dehydrated or lyophilized powder. Such formulations may be stored either in a ready to use form or requiring reconstitution immediately prior to administration. The preferred storage of such formulations is at temperatures at least as low as 4° C. and preferably at −70° C. It is also preferred that such formulations containing the active agents are stored and administered at or near physiological pH. It is presently believed that administration in a formulation at a high pH (i.e. greater than 8) or at a low pH (i.e. less than 5) is undesirable.

The manner of administering the pharmaceutical formulations containing the active agents for systemic delivery can be via subcutaneous, intramuscular, intravenous, oral, intranasal, or vaginal or rectal suppository. Preferably the manner of administration of the formulations containing active agents for local delivery is via intraarticular, intratracheal, or instillation or inhalations to the respiratory tract. In addition it may be desirable to administer the active agents to specified portions of the alimentary canal either by oral administration of the active agents in an appropriate formulation or device.

For oral administration, the pharmaceutical composition of the present invention is encapsulated. The encapsulated active agents can be formulated with or without pharmaceutically-acceptable carriers customarily used in the compounding of solid dosage forms. Preferably, the capsule is designed so that the active portion of the formulation is released at that point in the gastro-intestinal tract when bioavailability is maximized and pre-systemic degradation is minimized. Additional excipients may be included to facilitate absorption of the active agents. Diluents, flavorings, low melting point waxes, vegetable oils, lubricants, suspending agents, tablet disintegrating agents, and binders may also be employed.

Regardless of the manner of administration, the specific dose is calculated according to the approximate body weight of the patient. Other factors in determining the appropriate dosage can include the disease or condition to be treated or prevented, route of administration and the age, sex and medical condition of the patient. In certain embodiments, the dosage and administration is designed to create a preselected concentration range of CNTF in the patient's blood stream. Preferably, CNTF is administered in doses between about 0.0005 mg/kg and 1 mg/kg. Further refinement of the calculations necessary to determine the appropriate dosage for treatment involving each of the above mentioned formulations is routinely made by those of ordinary skill in the art and is within the ambit of tasks routinely performed by them without undue experimentation, especially in light of the dosage information and assays disclosed herein. These dosages may be ascertained through use of the established assays for determining dosages utilized in conjunction with appropriate dose-response data.

As described above, the dosage sufficient to deliver a "therapeutically effective amount" of CNTF can be determined by those of ordinary skill in the art without undue experimentation. A "therapeutically effective amount" may be defined as the amount of CNTF sufficient to treat impotency in the patient.

It should be noted that the CNTF formulations described herein may be used for veterinary as well as human applications and that the term "patient" should not be construed in a limiting manner. In the case of veterinary applications, the dosage ranges should be the same as specified above.

In studies relating to therapeutic uses of rhCNTF, it was observed that erectlie activity was stimulated in normal rats at seven to nine days after the initiation of daily subcutaneous dosing with rhCNTF. Other well-known erection-stimulating factors in both humans and rats, such as apomorphine, bromocryptine and vasoactive intestinal peptide, produce their effects at the first exposure to drug. In contrast, the rhCNTF used in the experiments induced a response after a more chronic exposure to the drug. The behavioral effects of rhCNTF are believed to be mediated by a peripheral or central neural mechanism rather than by direct effects on vascular, smooth muscle, or skeletal muscle tissues of the male reproductive system. The relative importance to the etiology of impotency of deterioration of the nerve supply compared with vascular or other dysfunctions is suggested by the observations that responses of erectile tissue taken from impotent men to neurotransmitters appear to be intact and that erections can be induced in many impotent men by injections into the corpus cavernosum of vasodilatory substances. The erection-enhancing properties of rhCNTF in normal rats is believed to relate to its ability to stimulate neuropeptide synthesis peripherally in penile nerves or to alter brain dopamine neurochemistry. It is further believed that either mechanism is distinct from the neurotrophic properties of CNTF and that therapy with CNTF to facilitate erectile responses in cases of impotency is therefore a novel use of the neurotrophic factor.

The administration of rhCNTF in vivo may enhance erectlie function in dysfunctional states by increasing the synthesis and release of these putative neuropeptide transmitters of penile erection. The vasoactive intestinal polypeptide (VIP) content and density of distribution of VIP-ergic fibers were reduced in cavernous tissue obtained from patients with organic impotency compared with normal controls and a decrease in VIP immunoreactivity was measured in general in nerves from diabetic subjects, a population with a high incidence of impotency. The intracavernous injection of VIP has previously been found to cause the transient restoration of potency in some patients.

There is evidence that CNTF alters neuropeptidergic transmission in peripheral nerves. In vitro, the addition of CNTF to primary neuronal cultures and to a neuroblastoma cell line induced mRNA for a number of neuropeptides including VIP, calcitonin-gene related peptide, substance P and somatostatin. In vivo, the administration of CNTF stimulated levels of substance P and calcitonin gene related peptide in sensory ganglia of both young and fully grown rats (Apfel et al., *Brain Res.*, 604:1–6 (1993)). CNTF has been localized to peripheral nerve tissue in adult animals, i.e., sciatic nerve, but has not been localized in penile nerves.

Since receptors for CNTF have been localized in skeletal muscle, it is believed that CNTF may directly influence the function of the ischiocavernosus and bulbocavernosus muscles and thereby influence sexual function. In one report, it was found that the administration of CNTF to neonatal female rats prevented the preprogrammed death of motoneurons of the spinal nucleus of the bulbocavernosus and the atrophy of the bulbocavernosus muscle, a sexually dimorphic, striated muscle which is active during copulation (Forger et al., *J. Neuroscience*, 13: 4720–4726, (1993)). Although the mechanism is not clear, the administration of androgen in the same model could be substituted for the administration of CNTF with similar effects on preventing motoneuronal death, but with the additional effect of enlarging spinal neurons. It is therefore unlikely that CNTF is promoting neuronal survival by a direct mechanism related to the stimulation of androgen activity. It is, however, possible that nerve-derived CNTF has a myotrophic effect on the bulbocavernosus muscle and that the expression of CNTF is under androgen regulation. Of course, the enhanced erectile activity stimulated by CNTF in the mature sexually intact rat cannot be explained by these myotrophic or neurotrophic properties.

It is understood that the application of teachings of the present invention to a specific problem or environment will be within the capabilities of one having ordinary skill in the art in light of the teachings contained herein. Examples of representative uses of the present invention appear in the following examples.

EXAMPLE 1

Weight Loss and Anorexia in Rats and Monkeys Treated with CNTF

Male Sprague Dawley rats weighing approximately 350 to 400 grams were injected subcutaneously every afternoon for 12 days with either rhCNTF (1 mg/kg), recombinant rat (rr)CNTF (1 mg/kg) or vehicle. Immediately following the injection, behavior was closely monitored for 2 hours. Rats were housed five rats to a cage throughout the experiment including the period of behavioral observations. In a preliminary observation of CNTF-injected rats, a change in sexual behavior occurred nine days after the initiation of the daily injections. Based on that preliminary assessment, a grading system for behavioral responses was developed. An erection was scored as a behavior response during which the rat sat in an upright position with the emergence of the glans penis and the distal penile shaft that was placed in the rat's mouth.

In the behavior response studies reported in Table 1 below, each experimental group (n=10) was given either rat CNTF or human CNTF at a dose of 1 mg/kg daily for 10 consecutive days. The control group (n=10) was given vehicle only (0.1% albumin, 0.28% Tween, 10 mM phosphate, 10 mM Tris, 205 mM NaCl, 10% v/v glycerol, pH 7.4). The period of observation was 2 hours. In Table 1, the number of responders are reported as the # incidence/group, where an incidence refers to an observed erection.

TABLE 1A

ERECTION SCORING - VEHICLE

| Day of injection | # incidences per group of 10 rats |
|---|---|
| 1 | 0 |
| 2 | 0 |
| 3 | 0 |
| 4 | 0 |
| 5 | 0 |
| 8 | 0 |
| 9 | 0 |
| 10 | 0 |

TABLE 1B

ERECTION SCORING - RAT rhCNTF

| Day of injection | # incidences per group of 10 rats |
|---|---|
| 1 | 0 |
| 2 | 0 |
| 3 | 0 |
| 4 | 0 |
| 5 | 3 |
| 8 | 0 |
| 9 | 6 |
| 10 | 3 |

TABLE 1C

ERECTION SCORING - HUMAN rhCNTF

| Day of injection | # incidences per group of 10 rats |
|---|---|
| 1 | 0 |
| 2 | 0 |
| 3 | 0 |
| 4 | 0 |
| 5 | 0 |
| 8 | 1 |
| 9 | 2 |
| 10 | 4 |

The foregoing description of the invention is exemplary for purposes of illustration and explanation. It will be apparent to those skilled in the art that changes and modifications are possible without departing from the spirit and scope of the invention. It is intended that the following claims be interpreted to embrace all such changes and modifications.

What is claimed is:

1. A method for inducing a penile erection in a male human comprising administering to said human a therapeutically effective amount of naturally occurring human CNTF, wherein the male human is responsive to treatment, and the CNTF is an erectogenic agent.

2. The method of claim 1, wherein said CNTF is administered subcutaneously.

3. The method of claim 1, wherein said CNTF is in substantially pure form.

4. The method of claim 1, wherein said CNTF is administered in a pharmaceutically acceptable carrier.

5. The method of claim 1 wherein the CNTF is recombinant CNTF.

* * * * *